US008852165B2

(12) United States Patent
Mackay, II et al.

(10) Patent No.: US 8,852,165 B2
(45) Date of Patent: Oct. 7, 2014

(54) ENDOLUMINAL DRUG DELIVERY DEVICES AND METHODS

(76) Inventors: Edward G. Mackay, II, Largo, FL (US); Jose I. Almeida, Miami, FL (US); Julian J. Javier, Naples, FL (US); Jihad A. Mustapha, Ada, MI (US)

( * ) Notice: Subject to any disclaimer, the term of this patent is extended or adjusted under 35 U.S.C. 154(b) by 185 days.

(21) Appl. No.: 13/162,426

(22) Filed: Jun. 16, 2011

(65) Prior Publication Data
US 2012/0323220 A1    Dec. 20, 2012

(51) Int. Cl.
*A61M 31/00*    (2006.01)

(52) U.S. Cl.
USPC .............. 604/507; 604/164.01; 604/164.13; 604/500

(58) Field of Classification Search
USPC ......... 604/164.01, 164.13, 500, 513, 507, 13, 604/5
See application file for complete search history.

(56) References Cited

U.S. PATENT DOCUMENTS

| 4,578,061 | A |   | 3/1986  | Lemelson |            |
|-----------|---|---|---------|----------|------------|
| 5,292,311 | A |   | 3/1994  | Cope     |            |
| 5,360,416 | A |   | 11/1994 | Ausherman et al. |    |
| 5,464,395 | A | * | 11/1995 | Faxon et al. | 604/103.02 |
| 5,499,975 | A |   | 3/1996  | Cope et al. |         |
| 5,693,029 | A |   | 12/1997 | Leonhardt |          |
| 5,769,868 | A |   | 6/1998  | Yock     |            |
| 6,283,951 | B1 |  | 9/2001  | Flaherty et al. |    |
| 6,447,477 | B2 |  | 9/2002  | Burney et al. |      |
| 6,685,648 | B2 |  | 2/2004  | Flaherty et al. |    |
| 6,692,466 | B1 |  | 2/2004  | Chow et al. |        |
| 6,926,692 | B2 |  | 8/2005  | Katoh et al. |       |
| 6,989,004 | B2 | * | 1/2006  | Hinchliffe et al. | 604/164.01 |
| 7,141,041 | B2 |  | 11/2006 | Seward   |            |
| 7,172,576 | B2 |  | 2/2007  | Sawa et al. |        |
| 7,377,910 | B2 |  | 5/2008  | Katoh et al. |       |
| 7,381,200 | B2 |  | 6/2008  | Katoh et al. |       |
| 7,879,011 | B2 |  | 2/2011  | Chang    |            |
| 2006/0106338 | A1 | * | 5/2006 | Chang ........................... 604/104 |
| 2006/0142747 | A1 | * | 6/2006 | Appling ......................... 606/15 |
| 2007/0129706 | A1 |   | 6/2007 | Katoh et al. |        |
| 2007/0299404 | A1 |   | 12/2007 | Katoh et al. |       |

OTHER PUBLICATIONS

Cordis® Outback® Re-Entry Catheter, Chronic Total Occlusion (CTO) Technologies brochure, Dec. 2008.

* cited by examiner

*Primary Examiner* — Emily Schmidt
(74) *Attorney, Agent, or Firm* — Kaplan Breyer Schwarz & Ottesen, LLP; Harry K. Ahn

(57) ABSTRACT

A device and method for delivering a drug from inside a body lumen to tissue surrounding the body lumen. An endoluminal drug delivery device includes a dual-lumen catheter for housing a guidewire and a needle connectable to a drug source. The guidewire exits the catheter through an opening at the distal end, and the needle exits the catheter through an exit port in the outer wall of the catheter. A distal portion of the catheter has a single lumen and includes a taper, allowing the distal tip to act as a dilator. The device optionally includes a catheter lumen splitter and/or a handpiece assembly. A method of delivering fluid to tissue surrounding a body lumen includes inserting a guidewire into the body lumen, tracking the device over the guidewire, deploying the needle through the exit port to the tissue, delivering fluid, and retracting the needle into the catheter.

13 Claims, 13 Drawing Sheets

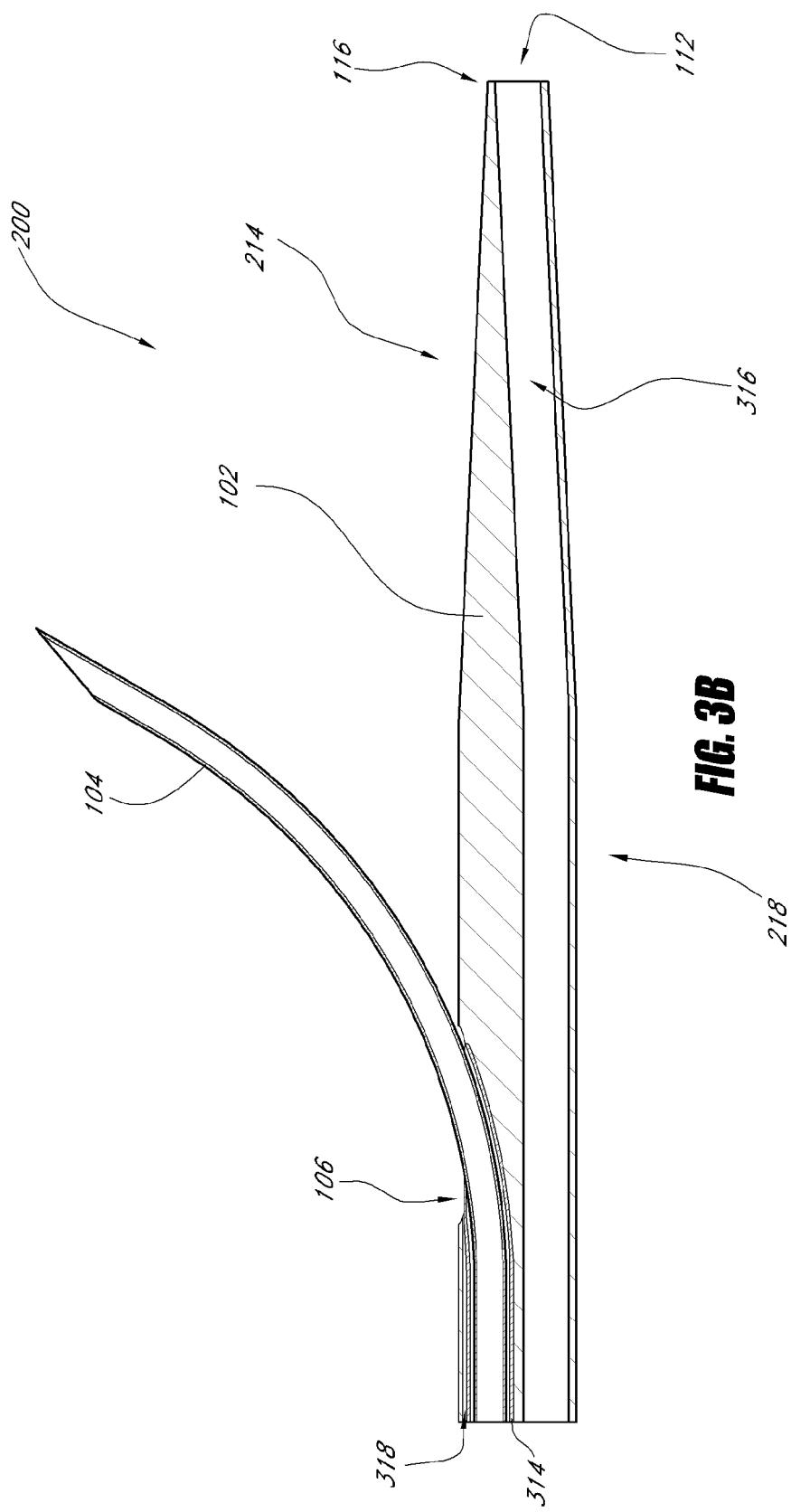

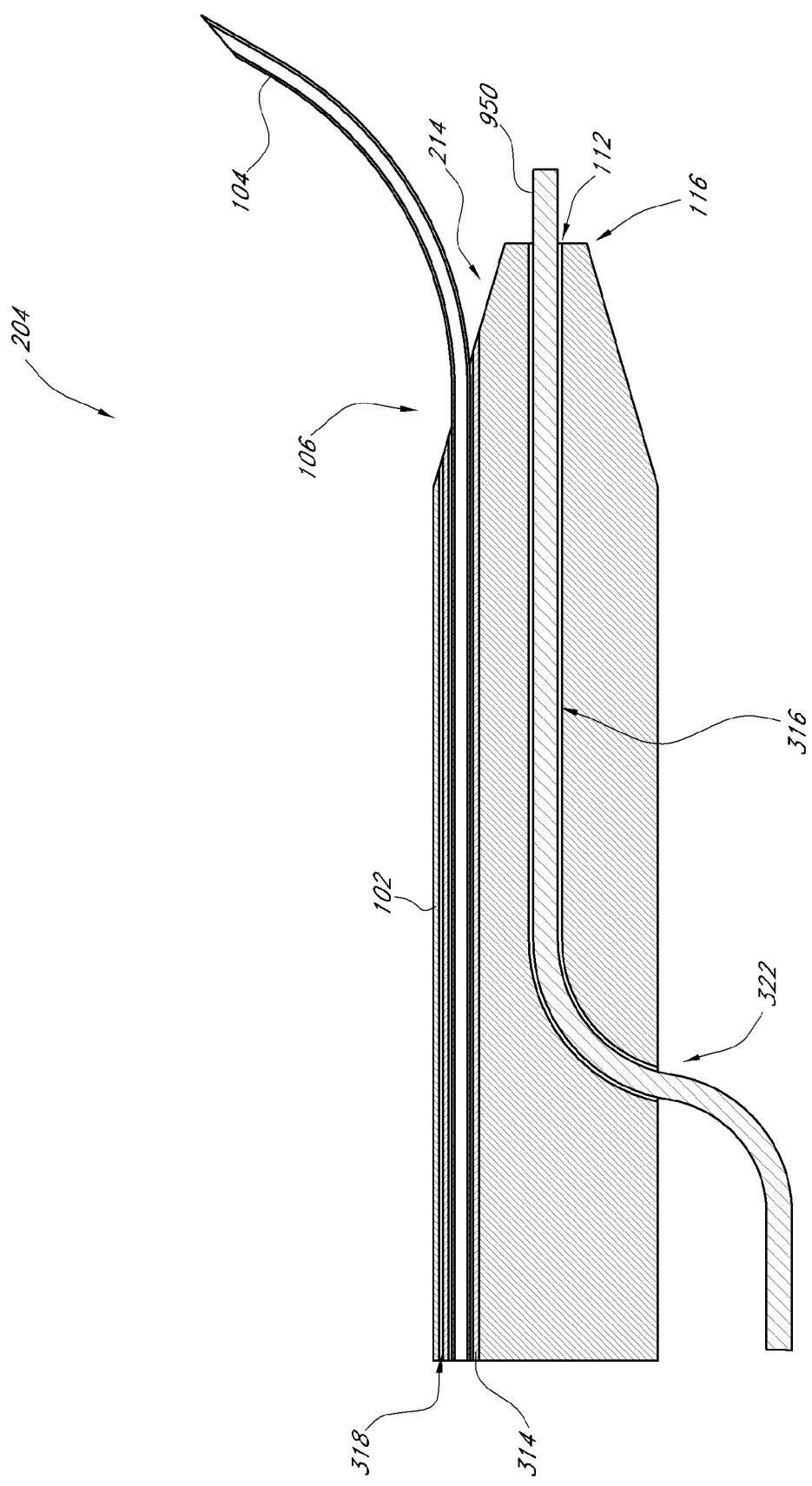

ENDOLUMINAL DRUG DELIVERY DEVICES AND METHODS

BACKGROUND

1. Field

The present application generally relates to devices and methods for delivering medicinal substances to an area surrounding a vein.

2. Description of the Related Art

Normally, valves in veins keep blood moving toward the heart and prevent backflow. In patients with varicose veins, the valves do not function properly, so blood flows back toward the patient's extremities and pools in the veins. This can lead to skin necrosis. Laser or RF ablation treatment creates hypercoagulability to close the abnormal vein, which is subsequently absorbed by the body. The current commonly-used method of delivering numbing medication to the treatment area prior to the ablation procedure requires multiple injections in the patient's thigh, each through the skin. Disadvantages of this method can include pain for the patient and inefficiency.

SUMMARY

The devices and methods described herein can use only a single puncture through the patient's skin to deliver multiple injections of a drug from inside a body lumen, such as a vein, to the tissue surrounding the body lumen. The endoluminal drug delivery device includes a flexible catheter with two lumens—a first lumen for a guidewire and a second lumen for a needle. The guidewire exits the catheter through an opening at the distal end, and the needle exits the catheter through an exit port in the catheter wall. The first lumen and guidewire can span the length of the catheter or only a distal portion of the catheter. The second lumen ends at the exit port, so the section of the catheter distal to the exit port has only one lumen and serves as a dilator. The catheter can have multiple exit ports along its length. A distal portion of the catheter can be tapered, and the exit port can be on the straight portion of the catheter or on the tapered portion. The second lumen houses a needle including a shape-memory material, such as nitinol, that is shape-set to have a curved distal portion. The needle straightens when inside the catheter, but when pushed forward in the catheter, the needle is configured to bias away from the second lumen and out of the exit port and assumes its curved shape. The catheter can split into two single-lumen portions at the proximal end of the catheter, and the device can have an optional lumen splitter to provide strength at the joint where the catheter splits. The device can also have an optional handpiece assembly with a button used to move the needle. The needle can be connected to a drug delivery system having a drug source. To use the device, the guidewire is inserted into a body lumen, such as a vein, through the patient's skin and the device is tracked over the guidewire by using the section of the catheter distal to the needle exit port as a dilator. Once the catheter is in position, the needle is pushed forward so that it exits the catheter through the exit port, pierces the body lumen wall, and enters the tissue surrounding the body lumen. The drug is delivered to the tissue from the drug source and delivery system, and then the needle is retracted back into the catheter. The device can then be further tracked over the guidewire to a different position, and the process can be repeated as desired.

In some embodiments, an endoluminal drug delivery device comprises a flexible catheter. The flexible catheter has a proximal end and a distal end. The device further comprises a first lumen extending from the proximal end to the distal end, a second lumen extending between the proximal end and an exit port, and a needle. The first lumen is adapted to house a guidewire. A section of the catheter distal to the exit port is self-dilating. The needle is configured to bias out of the exit port and away from the second lumen when the needle is longitudinally distally advanced. The needle includes a needle lumen configured to be in fluid communication with a drug delivery system.

In some embodiments, a method of delivering a fluid to tissue surrounding a body lumen having a wall comprises percutaneously inserting a guidewire into the body lumen through the wall and inserting a distal end of an endoluminal drug delivery device into the body lumen by tracking a first lumen of the device over the guidewire. The device includes a catheter having a proximal and a distal end. The first lumen extends from the proximal end to the distal end. The device further includes a second lumen extending between the proximal end and an exit port and a needle. A section of the catheter distal to the exit port is self-dilating during tracking. The needle is configured to bias away from the second lumen and out of the exit port when the needle is longitudinally distally advanced. When the exit port is in a first position, the needle is advanced out of the second lumen through the exit port. The method further comprises advancing the needle through the wall to the tissue, delivering fluid to the tissue through the needle, and retracting the needle into the catheter.

In some embodiments, a method of manufacturing an endoluminal drug delivery device comprises inserting a needle into a second lumen of a catheter. The catheter includes a first lumen extending from a proximal end to a distal end and is configured to house a guidewire and the second lumen extending between the proximal end and an exit port. A section of the catheter distal to the exit port is self-dilating. The needle is configured to bias out of the exit port and away from the second lumen when the needle is longitudinally distally advanced. The needle includes a needle lumen configured to be in fluid communication with a drug delivery system.

For purposes of summarizing the disclosure and the advantages achieved over the prior art, certain objects and advantages are described herein. Of course, it is to be understood that not necessarily all such objects or advantages need to be achieved in accordance with any particular embodiment. Thus, for example, those skilled in the art will recognize that the disclosure may be embodied or carried out in a manner that achieves or optimizes one advantage or group of advantages as taught or suggested herein without necessarily achieving other objects or advantages as may be taught or suggested herein.

All of these embodiments are intended to be within the scope of the disclosure herein. These and other embodiments will become readily apparent to those skilled in the art from the following detailed description having reference to the attached figures, the disclosure not being limited to any particular disclosed embodiment(s).

BRIEF DESCRIPTION OF THE DRAWINGS

These and other features, aspects, and advantages of the present disclosure are described with reference to the drawings of certain embodiments, which are intended to schematically illustrate certain embodiments and not to limit the invention.

FIG. 3B is a longitudinal cross-sectional view of the distal portion of the endoluminal drug delivery device of FIG. 3A;

FIG. 3D is an a longitudinal cross-sectional view of another example embodiment of a distal portion of an endoluminal drug delivery device;

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Figure 1:
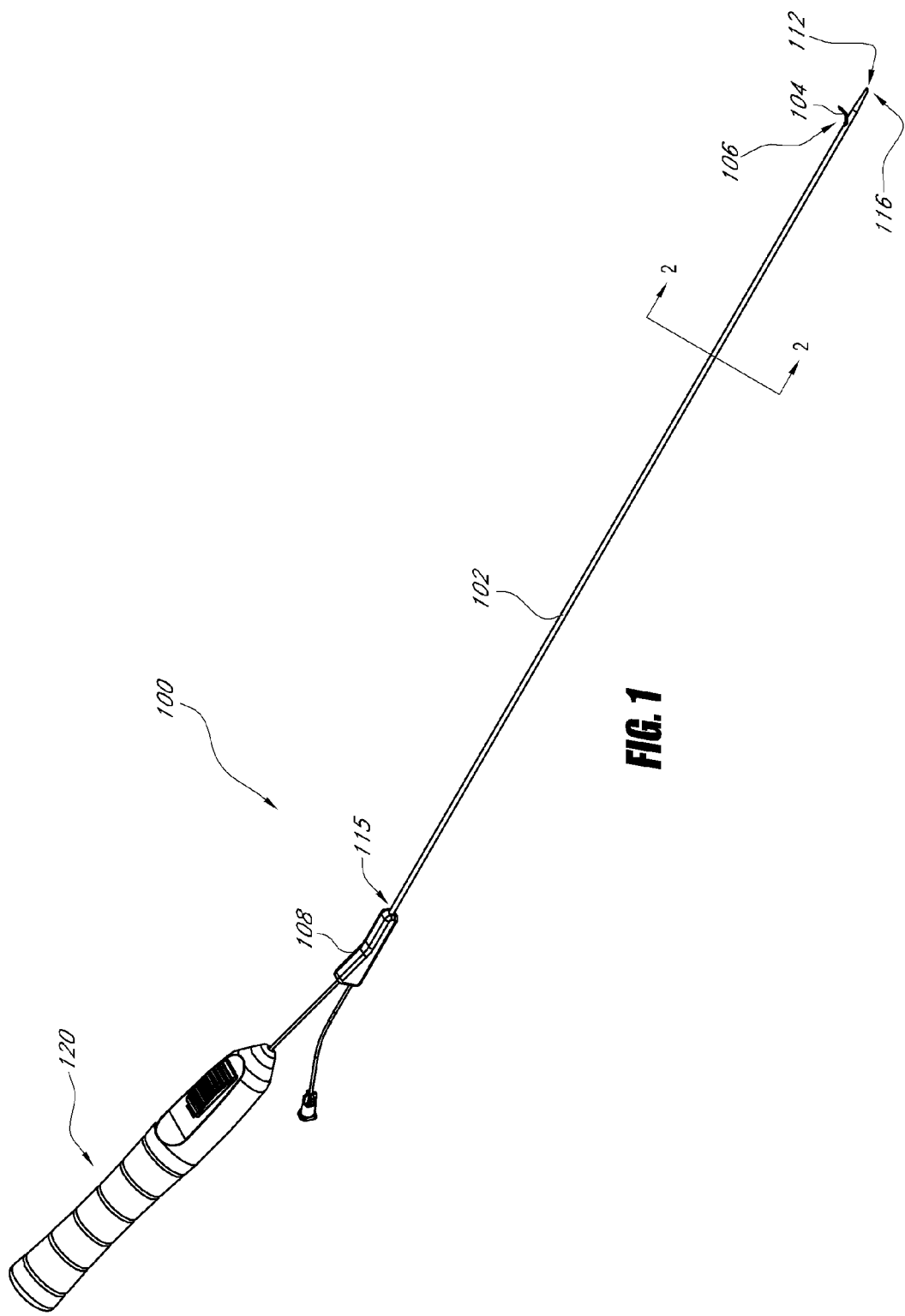
FIG. 1 is a top and side perspective view of an example embodiment of an endoluminal drug delivery device.
Figure 2:
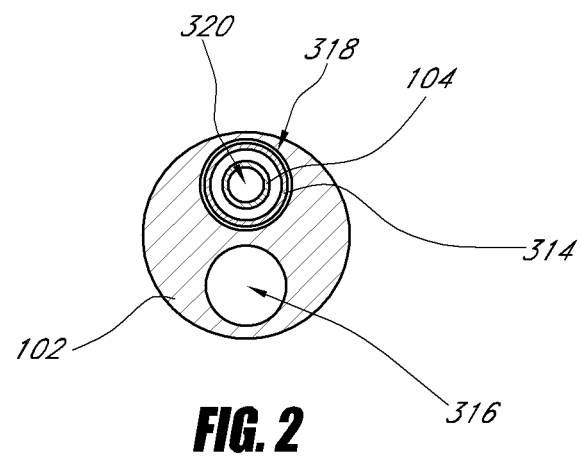
FIG. 2 is an example embodiment of a transverse cross-sectional view of the endoluminal drug delivery device of FIG. 1 along the line 2-2 in FIG. 1.

FIG. 1 illustrates an example embodiment of an endoluminal drug delivery device 100. FIG. 2 is an example embodiment of a transverse cross-sectional view of the device 100 of FIG. 1 along the line 2-2 in FIG. 1. The device 100 comprises a flexible catheter 102, a first lumen 316, a second lumen 318, and a needle 104. The flexible catheter 102 has a proximal end 115 and a distal end 116. The first lumen 316 extends from the proximal end 115 to the distal end 116. The first lumen 316 is configured to house a guidewire. The second lumen 318 extends between the proximal end 115 and an exit port 106. A section of the catheter 102 distal to the exit port 106 is self-dilating. The needle 104 is configured to bias out of the exit port 106 and away from the second lumen 318 when the needle 104 is longitudinally distally advanced. The needle 104 includes a needle lumen 320 configured to be in fluid communication with a drug delivery system. The guidewire exits the catheter 102 through an opening 112 at the distal end 116. In some embodiments, the device 100 comprises an optional catheter lumen splitter 108 and/or an optional handpiece assembly 120. The device 100 can be used, for example, to deliver a fluid such as a drug to tissue surrounding a blood vessel as described in greater detail herein.

In some embodiments, the catheter 102 has a length between about 45 cm and about 55 cm. Other lengths are also possible, for example based on needle size, guidewire size, intended use in different vasculature, for different patient sizes, etc. In some embodiments, the cross-sectional diameter of the catheter 102 is between about 0.090 inches (in.) and about 0.105 in. (approx. between about 0.23 centimeters (cm) and about 0.27 cm). Other diameters are also possible, for example based on needle size, guidewire size, intended use in different vasculature, for different patient sizes, etc. Other transverse cross-sectional profiles of the catheter are also possible (e.g., oblong, oval, egg-shaped, polygonal, etc.). The catheter 102 may comprise a flexible material so as to be maneuverable within a body lumen as described herein. For example, in some embodiments, the catheter 102 comprises a polymer (e.g., polyethylene). Other materials are also possible. The catheter 102 can be manufactured, for example, by extrusion, injection molding, or another suitable process.

FIG. 2 illustrates an embodiment in which the two lumens 316, 318 within the catheter 102 are in a parallel configuration. As described herein, the first lumen 316 is configured to house a guidewire, and the second lumen 318 is configured to house a needle 104. In some embodiments, the second lumen 318 houses a guide tube 314 between the lumen 318 wall and the needle 104, as shown in FIG. 2 and described in greater detail herein. In some embodiments, the first lumen 316 and the second lumen 318 have approximately the same diameter. In some embodiments, the first and second lumens have different diameters. The diameter of each lumen 316, 318 can be, for example, between about 0.025 in. and about 0.05 in. (approx. between about 0.064 cm and about 0.13 cm), between about 0.035 in. and about 0.045 in. (approx. between about 0.089 cm and about 0.11 cm) (e.g., about 0.039 in. (approx. about 0.099 cm)), combinations thereof, and the like. In some embodiments, the two lumens 316, 318 within the catheter 102 are in a different configuration. For example, the second lumen 318 can be oval or oblong to allow the needle 104 to flex within the lumen 318. For another example, the first lumen 316 and the second lumen 318 can both be oblong. For another example, at least one of the first lumen 316 and the second lumen 318 can be crescent-shaped. For still another example, the first lumen 316 and the second lumen 318 can be spaced semicircles. A wide variety of lumen configurations and shapes are possible, and the shapes of the lumens need not correspond to the shapes of the elements that the lumens are configured to contain.

Figure 3A:
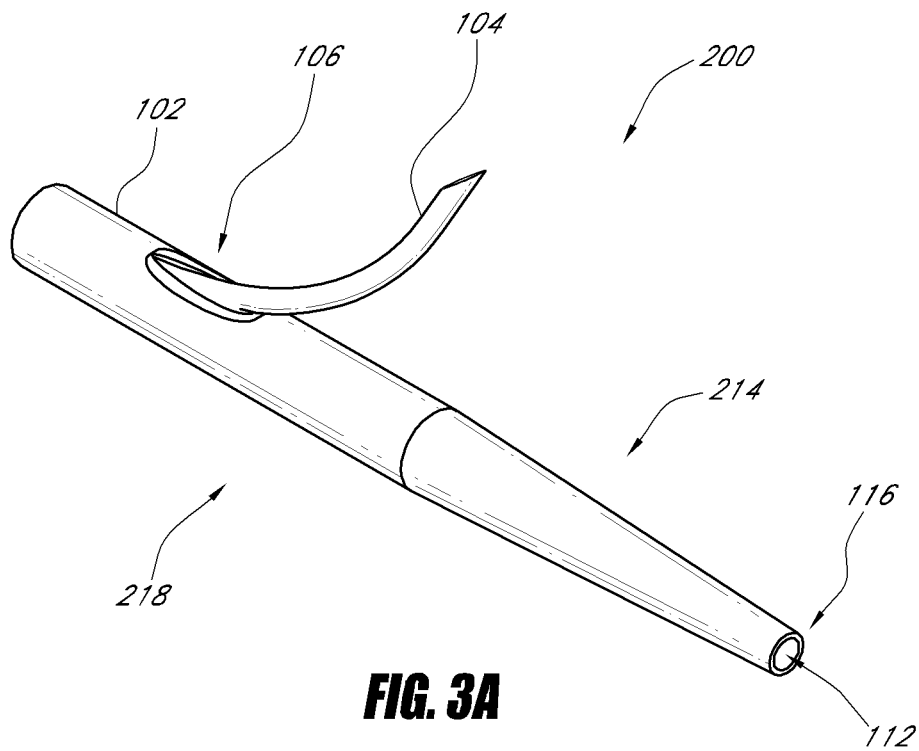
FIG. 3A is a top and side perspective view of an example embodiment of a distal portion of an endoluminal drug delivery device.

FIG. 3A illustrates an example embodiment of a distal portion 200 of the catheter 102 of the device 100. In some embodiments, the exit port 106 is proximate to the distal end 116 of the catheter 102. For example, the exit port 106 can be between about 0.6 in. and about 0.7 in. (approx. between about 1.5 cm and about 1.8 cm) from the distal end 116 of the catheter 102. Other distances of the exit port 106 from the distal end 116 are also possible, for example based on dilator length, taper portion angle if applicable, etc. In some embodiments, the exit port 106 has a length between about 0.20 in. and about 0.25 in. (approx. between about 0.51 cm and about 0.64 cm) and a width between about 0.029 in. and about 0.39 in. (approx. between about 0.073 cm and about 0.099 cm). Other exit port 106 dimensions are also possible, for example based on catheter size, needle size, etc.

FIG. 3B is a longitudinal cross-sectional view of the distal portion 200 of the catheter 102 of FIG. 3A. Because the second lumen 318 of the catheter 102 terminates at the exit port 106 proximal to the distal end 116 of the catheter 102, a single-lumen section 218 of the catheter 102 distal to the exit port 106 only contains the first lumen 316. In some embodiments, the single-lumen section 218 of the catheter 102 has a length from the distal edge of the exit port 106 to the distal end 116 of the catheter 102 of between about 0.5 in. and about 0.675 in. (between approx. 1.27 cm and about 1.72 cm). Other single-lumen section 218 lengths are also possible, for example based on dilator length, taper portion angle if applicable, etc. In some embodiments, the distal portion 200 of the catheter 102 includes a taper toward the distal end 116 (e.g., the outer diameter of the catheter 102 decreases from proximal to distal). In some embodiments, as illustrated in FIGS. 3A and 3B, a tapered portion 214 of the catheter 102 begins distal to the exit port 106, so the exit port 106 is on a straight side of the catheter 102. In some embodiments, the tapered portion 214 begins proximal to the exit port 106, so the exit port 106 is on the tapered portion 214 of the catheter 102, for example as illustrated in FIG. 3D. The single-lumen 316 housing a guidewire makes the section 218 of the catheter 102 distal to the exit port 106 sufficiently stiff so as to be pushable and allows the catheter 102 to follow the guidewire. The section 218 of the catheter 102 distal to the exit port 106 effectively serves as a dilator, making the catheter 102 self-dilating. In some embodiments, tapered features help guide the catheter 102 as the catheter 102 is tracked over the guidewire, contributing to the self-dilating nature of the catheter 102. Other shapes may also make the section 218 of the catheter 102 distal to the exit port 106 self-dilating.

Figure 3C:
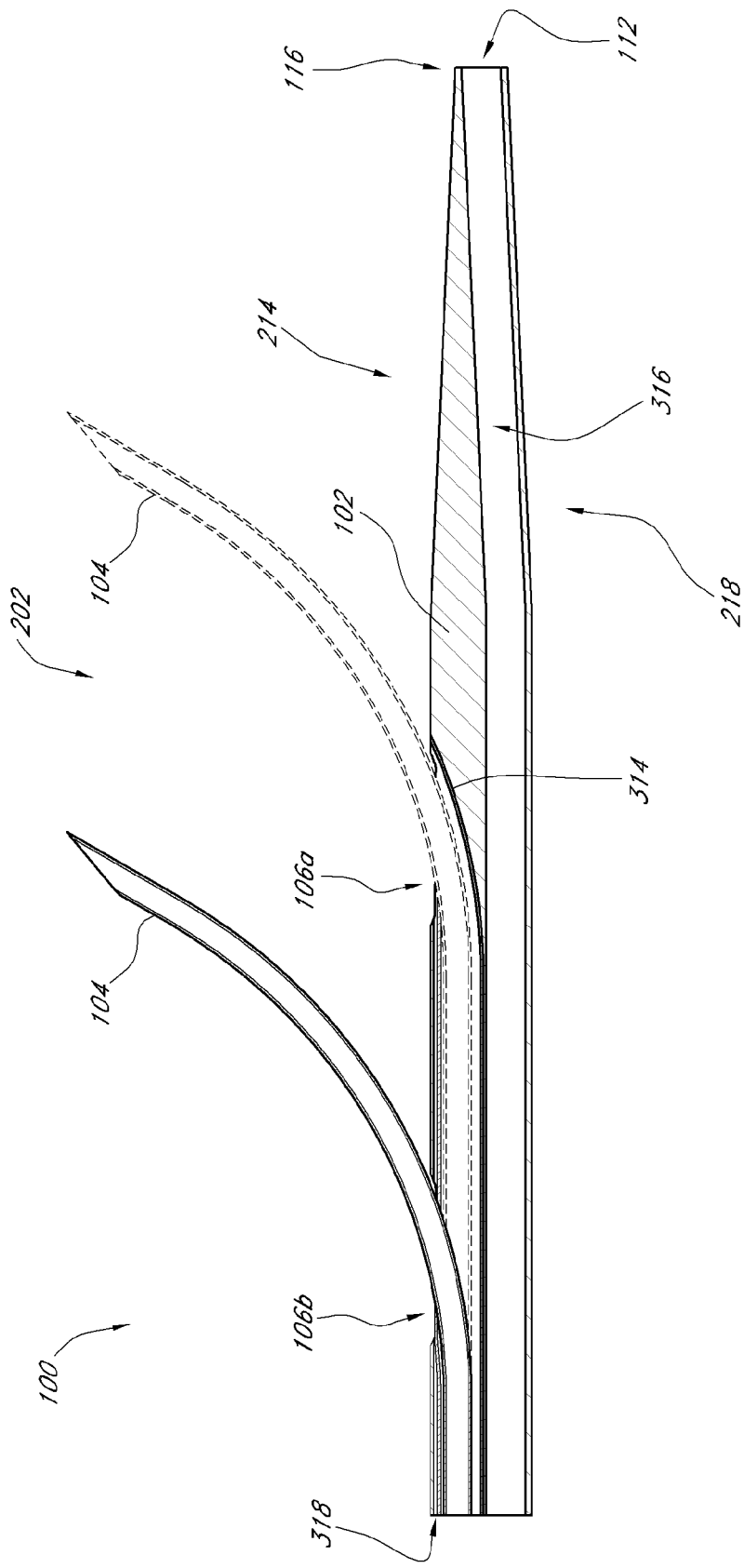
FIG. 3C is a longitudinal cross-sectional view of another example embodiment of a distal portion of an endoluminal drug delivery device.

FIG. 3C illustrates an embodiment of a distal portion 202 of the endoluminal drug delivery device 100 in which the catheter 102 includes a plurality of exit ports 106a, 106b. The needle 104 can be deployed from any of the exit ports 106a, 106b, depending on the position of the needle 104 within the catheter 102. In the embodiment illustrated in FIG. 3C, the exit port 106a is proximate to the distal end 116 of the catheter 102. In some embodiments, the distal tip of the needle 104 is initially between the most distal exit port 106a and the second exit port 106b proximal to the distal end 116 of the catheter 102. In some embodiments, the needle 104 can be longitudinally distally advanced to exit the most distal exit port 106a, after which the needle 104 can be longitudinally proximally advanced proximal to the exit port 106b, and then longitudinally distally advanced to exit the exit port 106b, and so on for any number of exit ports 106n (not shown) consecutively from distal to proximal. In certain such embodiments, the needle 104 can be used to make a plurality of injections at different longitudinal positions without movement of the guidewire 102. In some embodiments, the guidewire 102 is anchored in the vessel during movement of the needle 104. In some embodiments in which the needle 104 is rotatable within the catheter 102, the needle 104 can be rotated to bias away from the exit ports 106a, 106b (e.g., 180° or at least enough to not bias out of the exit ports 106a, 106b) during longitudinal movement when the needle 104 is not to exit the exit ports 106a, 106b, and can be rotated towards the exit ports 106a, 106b, and so on to exit port 106n (not shown). Combinations of the methods described herein are also possible. Although the exit ports 106a, 106b are illustrated in FIG. 3C as being circumferentially aligned, other circumferential arrangements are also possible.

FIG. 3D schematically illustrates an embodiment of a distal portion 204 of the endoluminal drug delivery device 100 in which the first lumen 316 extends from an opening 322 in the outer wall of the catheter 102 at a position proximal to the distal end 116 of the catheter 102 (e.g., from about 8 cm proximal to the distal end 116) to the distal end 116 of the catheter 102 in a so-called "rapid-exchange" configuration. In some embodiments, for example as illustrated in FIG. 3D, the first lumen 316 and second lumen 318 overlap so that a portion of the catheter 102 comprises both of the lumens 316, 318. The length of the overlapping portion can vary. In some embodiments, the first lumen 316 and second lumen 318 do not overlap within the catheter 102. In certain such embodiments, the catheter 102 has a smaller cross-sectional profile. The first lumen 316 has an opening 112 at the distal end 116 of the catheter 102. A guidewire 950 enters the first lumen 316 through the opening 112 at the distal end 116 of the catheter 102 and exits the catheter 102 through the opening 322 in the catheter 102. The guidewire 950 extends exterior to and alongside the catheter 102 proximal to the opening 322 in the catheter 102. In some embodiments, for example as illustrated in FIG. 3D, the opening 322 is along a straight portion of the catheter 102 proximal to the tapered portion 214. In some embodiments, the opening 322 is along the tapered portion 214 or the taper-straight junction.

FIG. 3D also schematically illustrates an embodiment of a distal portion 204 of the endoluminal drug delivery device 100 in which the exit port 106 is along the tapered portion 214. The second lumen 318 and the optional guide tube 314 are straight, and the needle 104 only curves once the distal portion has exited the exit port 106. Certain such embodiments may advantageously simplify manufacturing, for example because the guide tube 314 does not include a Tuohy-style tip and/or because the second lumen 318 is a bore. The needle 104 may bias when extended out of the exit port 106 without a deflection surface. In some embodiments, a distal portion 204 in which the exit port 106 is on the tapered portion does not include a guide tube, for example because the needle 104 does not distally extend towards a portion of the catheter 102.

In some embodiments (e.g., as described with respect to FIGS. 3B and 3C), the tapered portion 214 of the catheter 102 terminates distal to the exit port 106, so the exit port 106 is on a straight side of the catheter 102 in combination with a rapid-exchange guidewire configuration. FIG. 3D is schematic, and the relative dimensions, positions, angles, etc. therein may be modified to suit a desired configuration. For example, the length and angle of the tapered portion 214 can vary, the shape of the first lumen 316 can vary, etc. Other distal sections of the catheter 102 are also possible, including combinations of embodiments described herein and otherwise.

Figure 4:
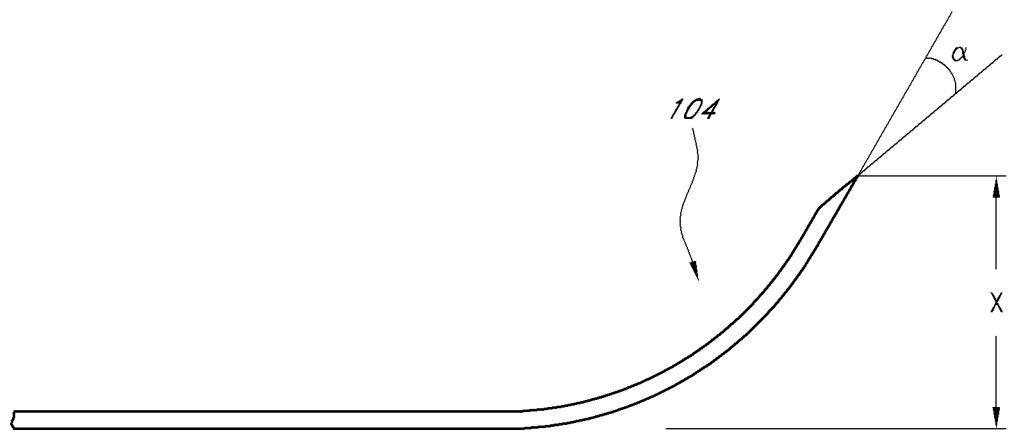
FIG. 4 is a side elevational view of an example embodiment of the distal portion of a needle.

FIG. 4 shows an example embodiment of a distal portion of the needle 104. In some embodiments, the needle 104 comprises (e.g., is made of) a shape-memory material, for example, nitinol. In certain embodiments, the needle 104 is shape-set so that the distal portion is curved when the needle 104 is not restrained (e.g., within the second lumen 318 of the catheter 102, within the guide tube 314, etc.). The distal portion of the needle 104 may be substantially straight when the needle 104 is confined in the second lumen 318 of the catheter 102. When unrestrained, the curve of the distal portion of the needle 104 can have a radius of curvature between about 0.45 in. and about 0.55 in. (approx. between about 1.14 cm to about 1.40 cm). Other radii of curvature and distal portion shapes of the needle 104 are also possible, for example based on dimensions of the catheter 102, the vasculature, the patient, etc. The needle 104 can have an inner cross-sectional diameter between about 0.015 in. and about 0.025 in. (approx. between about 0.038 cm and about 0.064 cm) and an outer cross-sectional diameter between about 0.02 in. and about 0.03 in. (approx. between about 0.05 cm and about 0.08 cm), and can have a length between about 20 in. and about 30 in. (approx. between about 50 cm and about 76 cm). Other dimensions of the needle 104 are also possible, for example based on dimensions of the catheter 102, the vasculature, the patient, etc.

When the distal end of the needle 104 exits the exit port 106 of the catheter 102, for example as shown in FIG. 3A, the distal end of the needle 104 self-assumes a curved shape without requiring influence, for example, from a deflection surface in the second lumen 318. The needle 104 is thereby configured to bias out of the exit port 106 and away from the catheter 102 when the needle 104 is longitudinally distally advanced within the second lumen 318. In some embodiments, the catheter 102 comprises a deflection surface (e.g., a surface of the guide tube 314 or other surface). In certain such embodiments, the deflection surface comprises a planar surface, a curved surface, combinations thereof, and the like. Although the needle 104 is configured to bias out of the exit port 106 without a deflection surface, a deflection surface may help to protect interior surfaces of the catheter 102 from the tip of the needle 104, may help guide a rotatable needle 104 to the exit port 106, etc. Referring again to FIG. 4, in some embodiments, in an unrestrained state, the distal tip of the needle 104 is spaced from a longitudinal axis defined by a straight portion of the needle 104 on the side of the needle 104 opposite the curve by a distance x of between about 0.35 in. and about 0.40 in. (approx. between about 0.89 cm and about 1.02 cm). Other distances x are also possible, for example depending on the size of the needle 104, the relative sizes of the vasculature and the catheter 102, etc.

The distal tip of the needle 104 is configured to pierce the vein wall and surrounding tissue. In some embodiments, the distal tip of the needle 104 has a bevel angle α between about 10° and about 30°, between about 15° and about 25° (e.g., about 20°), combinations thereof, and the like. Other bevel angles α are also possible. In some embodiments, the distal tip of the needle 104 has a conical or pencil point tip. In certain such embodiments, the distal tip of the needle 104 has a cone angle between about 10° and about 30°, between about 15° and about 25° (e.g., about 20°), combinations thereof, and the like. Other cone angles are also possible. Other configurations of the distal tip of the needle 104 are also possible. For example, the needle 104 may include sidewall apertures, apertures configured to spray fluid, etc. The needle 104 comprises a needle lumen 320 configured to be in fluid communication with a drug delivery system, and fluid can be delivered out of the tip of the needle 104.

In some embodiments, a method of manufacturing the endoluminal drug delivery device 100 comprises inserting the needle 104 into the second lumen 318 of the catheter 102. In some embodiments, the method of manufacturing comprises shape setting (e.g., heat setting) the distal portion of the needle 104 into a curved or other configuration. In some embodiments, the method of manufacturing comprises shaping the distal tip of the needle 104 into a beveled or pencil point tip (e.g., by laser cutting, grinding, chemical etching, etc.).

In some embodiments, for example as shown in FIG. 2, the second lumen 318 optionally comprises (e.g., is at least partially lined with) a guide tube 314. The guide tube 314 can comprise (e.g., be made of), for example, 304 stainless steel hypodermic tubing. Other materials are also possible. The distal end of the guide tube 314 can comprise a modified Tuohy-style tip with a radius between about 0.47 in. and about 0.53 in. (approx. between about 1.19 cm and about 1.35 cm). Other radii of Tuohy-style tips of the guide tube 314 are also possible, for example based on the shape of the distal portion of the needle 104, catheter dimensions, etc. A Tuohy-style distal tip of the guide tube 314 can be substantially aligned with the exit port 106 so that the needle 104 can exit the guide tube 314 and the catheter 102 through the exit port 106 as described in greater detail herein. The Tuohy-style tip of the guide tube 314 can serve as a deflection surface (e.g., as described herein) for the needle 104 to protect the interior of the catheter 102 as the needle 104 exits the catheter 102 through the exit port 106. In some embodiments, the guide tube 314 can be 20 gauge and have an outside cross-sectional diameter between about 0.03 in. and about 0.4 in. (approx. between about 0.076 cm and about 0.102 cm) and an inside cross-sectional diameter between about 0.025 in. and about 0.035 in. (approx. between about 0.064 cm and about 0.089 cm). Other dimensions of the guide tube 314 are also possible, for example based on dimensions of the needle 104, dimensions of the catheter 102, etc. In some embodiments, the guide tube 314 is adhered to the interior wall of the second lumen 318. In some embodiments, the guide tube 314 is inserted into the second lumen 318. In certain such embodiments, the shape of the guide tube 314 causes the guide tube 314 to remain properly positioned within the lumen 318. In some embodiments, the guide tube 314 extends from the proximal end 115 to the exit port 106. In certain such embodiments, the guide tube 314 can have a length of about 22 in.±about 0.03 in. (approx. about 56 cm±about 0.076 cm). In some embodiments, only a portion, for example, about 0.5 in. to about 1.5 in. (approx. about 1.3 cm to about 3.8 cm) of the second lumen 318 proximate to the exit port 106 comprises a guide tube 314. Other lengths of the guide tube 314 are also possible (e.g., corresponding to the length of a straightened distal portion of the needle 104).

In some embodiments, the guide tube 314 is cut (e.g., laser cut) to maintain the flexibility of the catheter 102. The guide tube 314 can advantageously add strength to the catheter 102, inhibiting (e.g., preventing) torque, deformation of the distal portion 200 that may be caused by the curved shape of the distal portion of the needle 104, and/or skiving or other damage near the exit port 106 caused by the needle 104. The guide tube 314 may also beneficially keep the curved distal portion of the needle 104 straight while the distal portion of the needle 104 is inside the catheter 102 and/or allow the needle 104 to move more freely within the catheter 102 as compared to movement of a needle 104 in a plastic, which may for example soften if heated to body temperature. In some embodiments, a method of manufacturing an endoluminal drug delivery device 100 comprises inserting the guide tube 314 into the second lumen 318. In some embodiments, a method of manufacturing the device 100 comprises cutting (e.g., laser cutting) and/or shaping the guide tube 314. Other support structures (e.g., a coil, a braid) are also possible to have some of the advantages described herein.

Figure 5A:
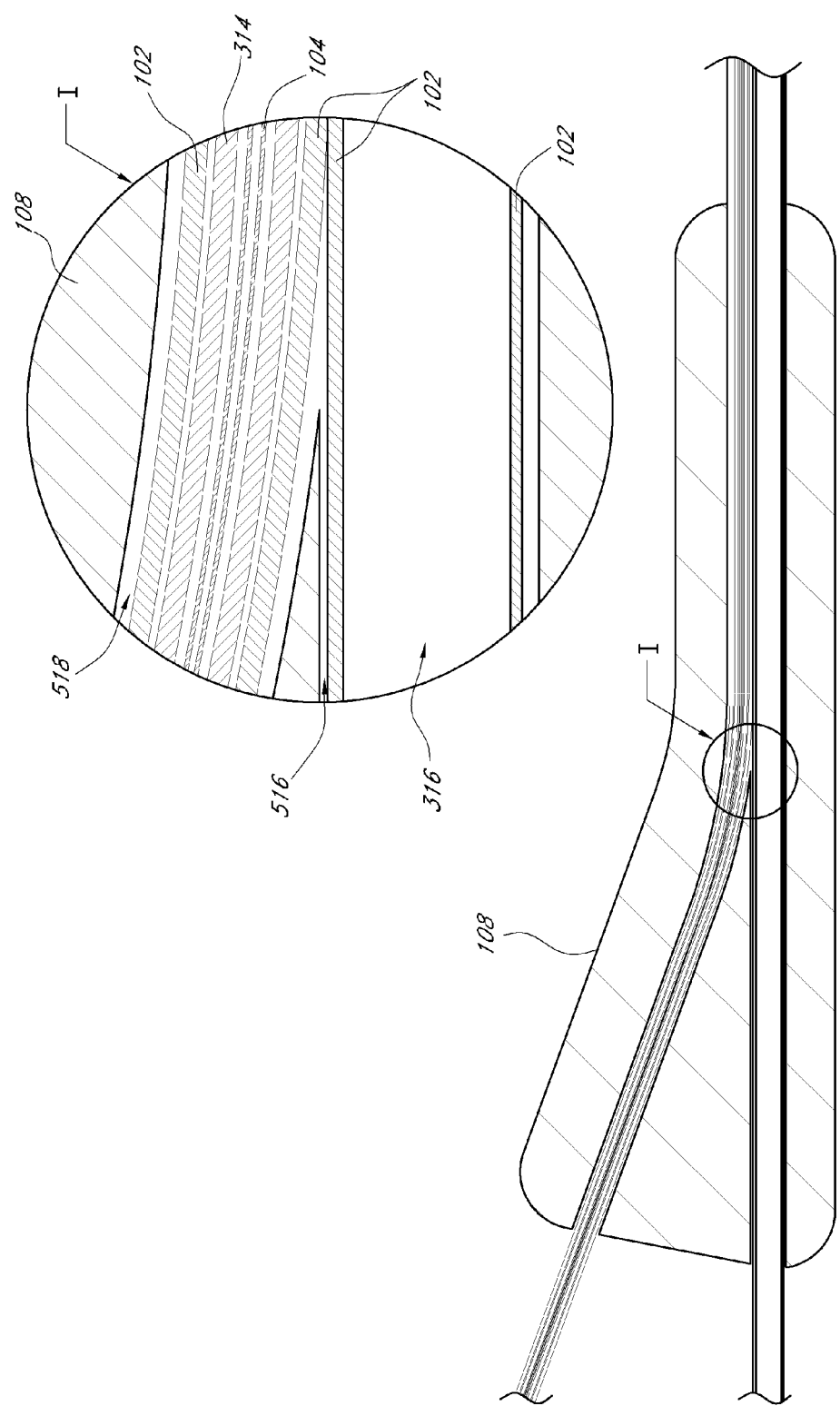
FIG. 5A is a longitudinal cross-sectional view of an example embodiment of a catheter lumen splitter including a portion enlarged for clarity.

In some embodiments, the device 100 optionally includes a catheter lumen splitter or Y-connector 108 coupled to the catheter 102 proximate to the proximal end 115 of the catheter 102. In some embodiments, a method of manufacturing an endoluminal drug delivery device 100 comprises coupling a lumen splitter 108 to the catheter 102. In some embodiments, the splitter 108 has a length between about 1 in. and about 2 in. (approx. between about 2.5 cm and about 5.0 cm). Other lengths are also possible (e.g., depending on the dimensions of the catheter 102, the amount of split desired, etc.). In some embodiments, the splitter 108 comprises high density polyethylene (HDPE). Other materials are also possible. In some embodiments, the splitter 108 comprises a first lumen 516 and a second lumen 518. In some embodiments, the first and second lumens 516, 518 of the splitter 108 converge toward the distal end of the splitter 108 to form a single lumen. In some embodiments, for example as shown in FIG. 5A, as the catheter 102 passes through the lumen splitter 108 from a distal end of the lumen splitter 108 to a proximal end of the lumen splitter 108, the catheter 102 separates into two single lumen components. The splitter 108 may advantageously provide strength at the joint where the catheter 102 separates. In some embodiments, a portion of the catheter 102 comprising the first lumen 316 passes through the first lumen 516 of the splitter 108 and extends beyond the proximal end of the lumen splitter 108 by about 4.5 in. to about 5.5 in. (approx. about 11.4 cm to about 14 cm). In some embodiments, a proximal end of the portion of the catheter 102 comprising the first lumen 316 comprises a fitting, for example a Luer fitting (e.g., as illustrated in FIG. 1). In some embodiments, the portion of the catheter 102 comprising the first lumen 316 does not extend beyond the proximal end of the lumen splitter 108, and the proximal end of the splitter 108 comprises a fitting, for example a Luer fitting.

Figure 5B:
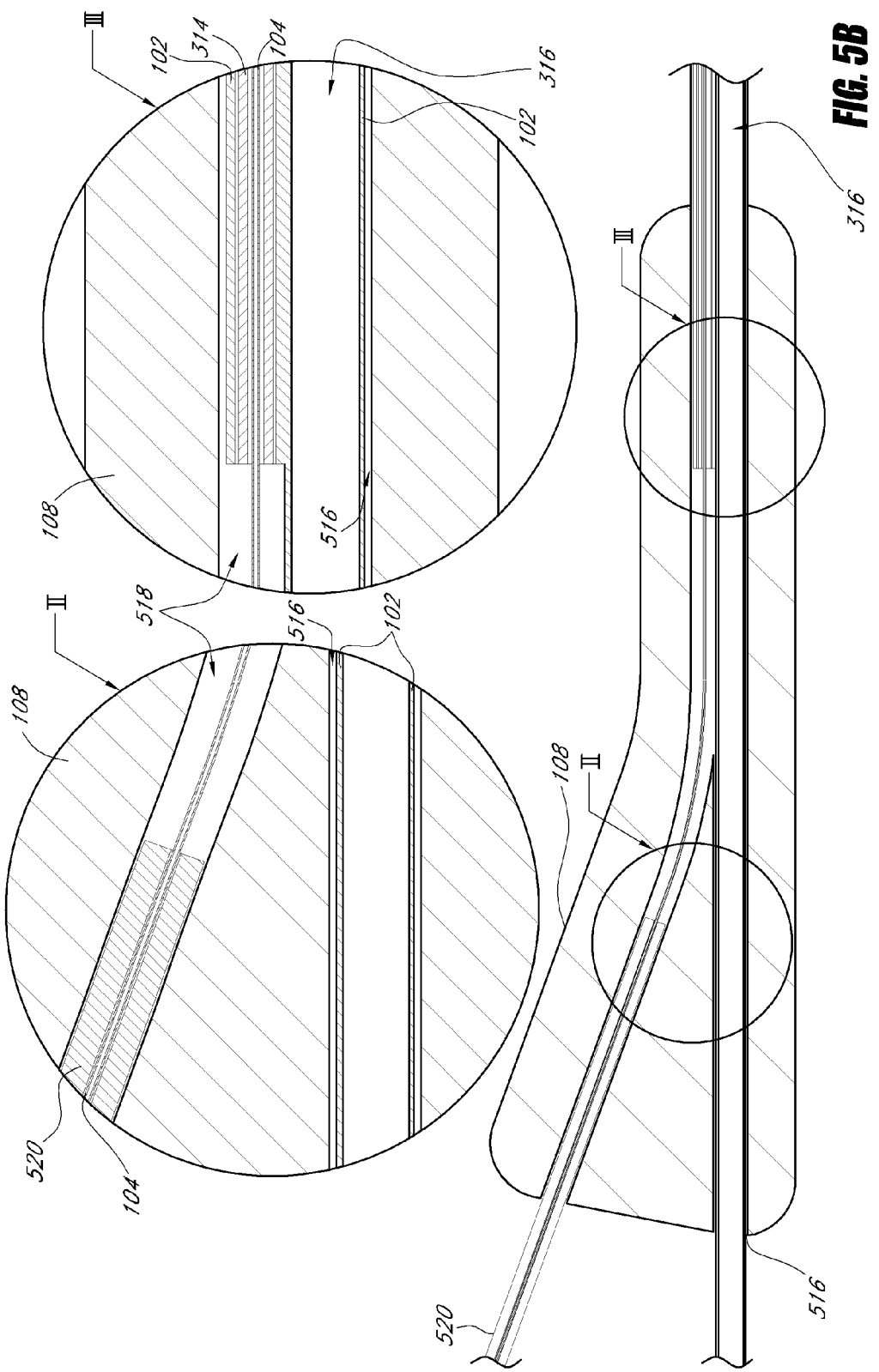
FIG. 5B is a longitudinal cross-sectional view of another example embodiment of a catheter lumen splitter including two portions enlarged for clarity.

In some embodiments, the needle 104 and a portion of the catheter 102 comprising the second lumen 318 pass through the second lumen 518 of the splitter 108 and extend about 3 in. (approx. about 7.6 cm) beyond the proximal end of the splitter 108, for example for coupling to a handpiece assembly 120. In some embodiments, the guide tube 314 can also pass through the second lumen 518 of the splitter 108 and extend beyond the proximal end of the splitter 108, for example for coupling to a handpiece assembly 120. In some embodiments, for example as shown in FIG. 5B, the guide tube 314 terminates within the splitter 108 and does not extend beyond the proximal end of the splitter 108. In some embodiments, for example as shown in FIG. 5B, the portion of the catheter 102 comprising the second lumen 318 terminates within the splitter 108. In certain embodiments, a separate piece of catheter tubing 520 may optionally be attached (e.g., welded, glued, adhered, mechanically crimped, mechanically swaged, combinations thereof, and the like) to the proximal end of the splitter 108 in fluid communication with the second lumen 518 of the splitter 108 and surrounding the needle 104. In some embodiments, a method of manufacturing comprises attaching (e.g., welding, gluing, adhering, mechanically crimping, mechanically swaging, combinations thereof, and the like) a separate piece of catheter tubing 520 to the proximal end of the splitter 108 in fluid communication with the second lumen 518 of the splitter 108 and surrounding the needle 104.

The lumens 516, 518 of the splitter 108 and/or proximal sections of the needle 104, guide tube 314, and/or catheter 102 can be configured to angle away from the longitudinal axis of the catheter 102. For example, a proximal portion of the portion of the catheter 102 comprising the first lumen 316 can angle away from the longitudinal axis of the catheter 102 in a first direction at an angle β to spatially separate the first lumen 316 of the catheter 102 from the second lumen 318 of the catheter 102 and/or to allow easier manipulation of a guidewire in the first lumen 316 of the catheter 102. In some embodiments, the angle β is between about 10° and about 30°, between about 15° and about 25° (e.g., about 20°), combinations thereof, and the like. Other angles β are also possible, for example depending on the guidewire to be used (e.g., amount of manipulation room preferred for a guidewire, maximum bending angle for a guidewire, etc.). For another example, proximal portions of the second lumen 518 of the splitter 108, needle 104, guide tube 314, and/or portion of the catheter 102 comprising the second lumen 318 can angle away from the longitudinal axis of the catheter 102 in a second direction (e.g., opposite to the first direction) at an angle γ to spatially separate the first lumen 316 of the catheter 102 from the second lumen 318 of the catheter 102 and/or to allow easier manipulation of a handpiece assembly 120. In some embodiments, the angle γ is between about 10° and about 30°, between about 15° and about 25° (e.g., about 20°), combinations thereof, and the like. Other angles γ are also possible, for example depending on the handpiece assembly 120 to be used (e.g., amount of manipulation room preferred for the handpiece assembly 120), the needle 104 (e.g., maximum bending angle for the needle 104), etc. Separation of the first and second lumens 316, 318 of the catheter 102 may advantageously allow for improved maneuverability of the various components of the device 100 during use.

Figure 6A:
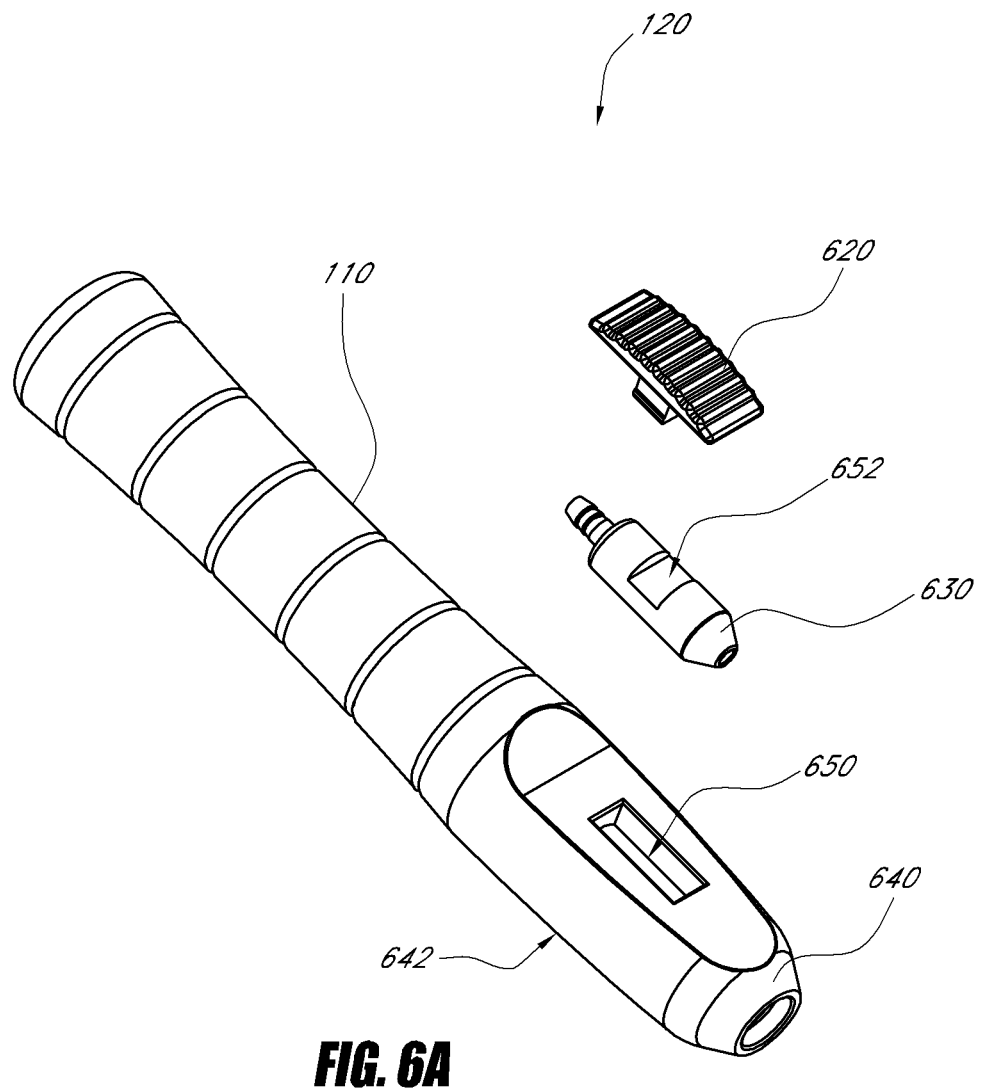
FIG. 6A is an exploded top and side perspective view an example embodiment of a handpiece assembly.
Figure 6B:
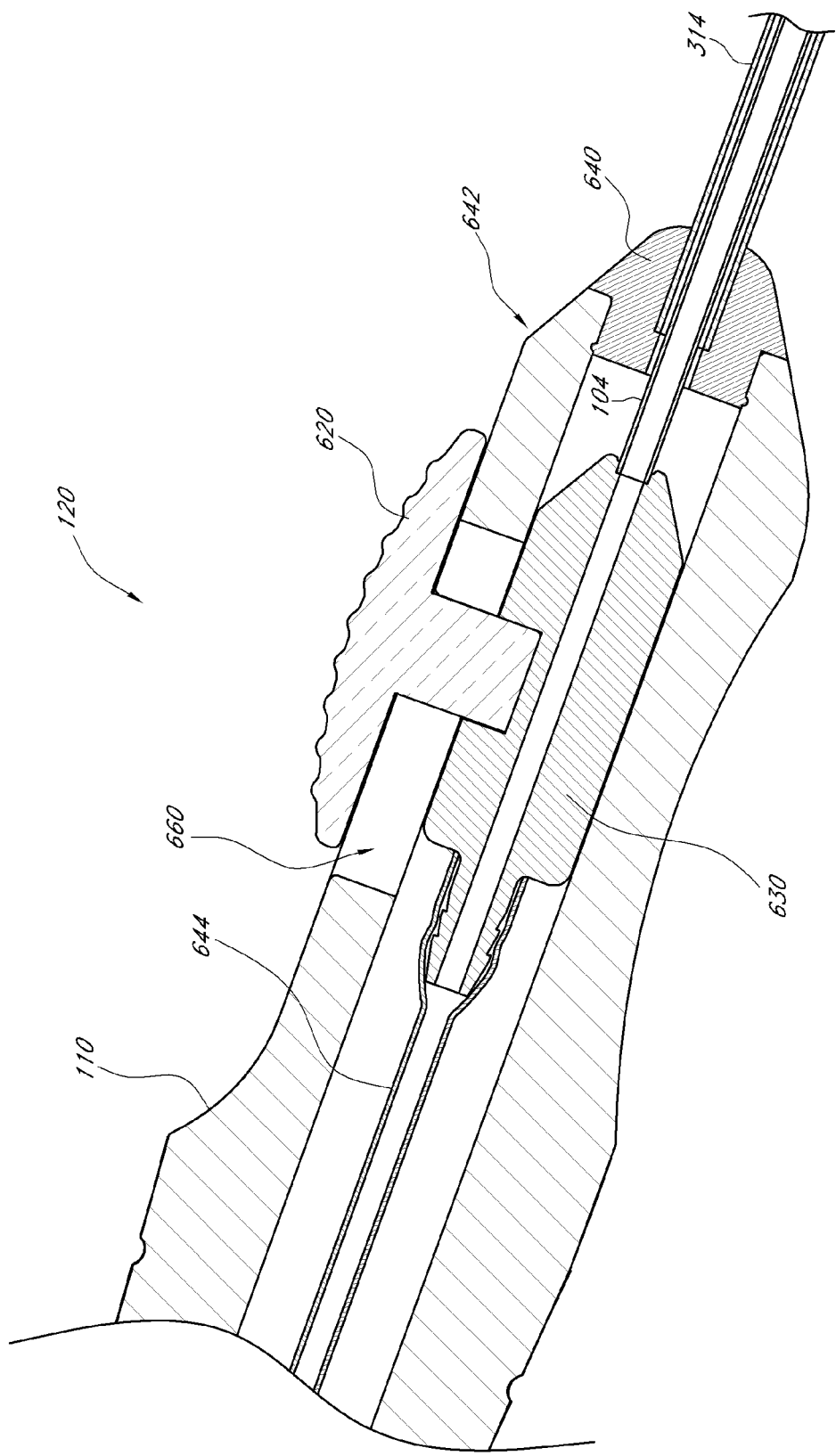
FIG. 6B is a longitudinal cross-sectional view of the assembled handpiece assembly of FIG. 6A.

In some embodiments, the endoluminal drug delivery device 100 optionally includes a handpiece assembly 120. FIG. 6A shows an exploded view of the handpiece assembly 120, and FIG. 6B shows a longitudinal cross-sectional view of the assembled handpiece assembly 120. The handpiece assembly 120 comprises a handle 110, a driver 630, and a button 620. The handle 110 can be coupled to the proximal end of the portion of the catheter 102 comprising the second lumen 318, for example extending proximal to a lumen splitter 108 as shown in FIG. 5A or otherwise. In some embodiments, the handle 110 is coupled to a separate piece of catheter tubing 520 attached to the proximal end of a splitter 108 in fluid communication with the second lumen 518 of the splitter 108 as shown in FIG. 5B. Other connections are also possible (e.g., embodiments in which the device 100 does not comprise a lumen splitter 108). In some embodiments, the handle 110 is coupled to the guide tube 314. In some embodiments, the handle 110 is coupled to or integrated with a splitter 108. The handle 110 may optionally comprise a separate distal piece or nose 640 that is attached (e.g., welded, glued, adhered, mechanically crimped, mechanically swaged, combinations thereof, and the like) to the main body 642 of the handle 110. In some embodiments, the nose 640 is integral with the main body 642 of the handle 110 and is not a separate component. Constructing the handle 110 with a separate nose 640 may advantageously allow for easier manufacturing and/or assembly of the handpiece assembly 120, allow rotation (e.g., ratcheting) of the needle 104 relative to the catheter 102, etc. Constructing the handle 110 with the nose 640 integral to the main body 642 may advantageously reduce the number of pieces, reduce assembly complexity, and/or reduce the likelihood of the pieces separating during use.

When assembled, the driver 630 of the handpiece assembly 120 is inside the handle 110. The button 620 is inserted into a cutout 650 in the top of the handle 110 and snaps into a notch 652 in the top of the driver 630. Other connections between the button 620 and the driver 630 are also possible (e.g., adhering). The proximal end of the needle 104 is attached to the distal end of the driver 630, for example with adhesive (e.g., Class VI epoxy), over molding, and/or other coupling techniques. The driver 630 translates movement of the button 620 into movement of the needle 104. The button 620 is used to distally longitudinally extend and proximally longitudinally retract the needle 104 within the catheter 102, and to cause the needle 104 to extend out of the exit port 106 and to retract into the exit port 106. In some embodiments, the needle 104 is rotationally fixed relative to the catheter 102, for example due to the catheter 102 being fixed to the lumen splitter 108 and handle 110. In some embodiments, the button 620 slides in a track 660 and longitudinal movement of the button 620 causes 1:1 longitudinal movement of the needle 104 within the second lumen 318 of the catheter 102. In some embodiments, no handpiece assembly 120 is used, and instead the proximal end of the needle 104 is directly manipulated.

In some embodiments, a method of manufacturing the device 100 includes assembling the handpiece assembly 120 and coupling the handpiece assembly 120 to the device 100. For example, the driver 630 may be placed in the distal end of the handle 110 and rotated until the notch is aligned with the cutout 650. The driver 630 may then be coupled to the button 620 and the needle 104. In some embodiments, a method of manufacturing comprises coupling the handpiece assembly 120 (e.g., the handle 110 or the nose 640 of the handle 110) to the catheter 102, the lumen splitter 108, a tube 520, etc.

In some embodiments, an endoluminal drug delivery system comprises the endoluminal drug delivery device 100 and tubing 644 configured to fluidly couple the needle lumen to a drug delivery system. The distal end of the tubing 644 can be coupled to the proximal end of the driver 630 in the handle 110, for example via a Luer fitting, a barb setting (e.g., as illustrated in FIG. 6B), etc., and the proximal end of the tubing 644 can be coupled to the drug delivery system. The tubing can comprise, for example, PVC tubing. The tubing may comprise a flexible material so that the movement of the needle 104 does not necessarily cause movement of the drug delivery system.

Figure 7A:
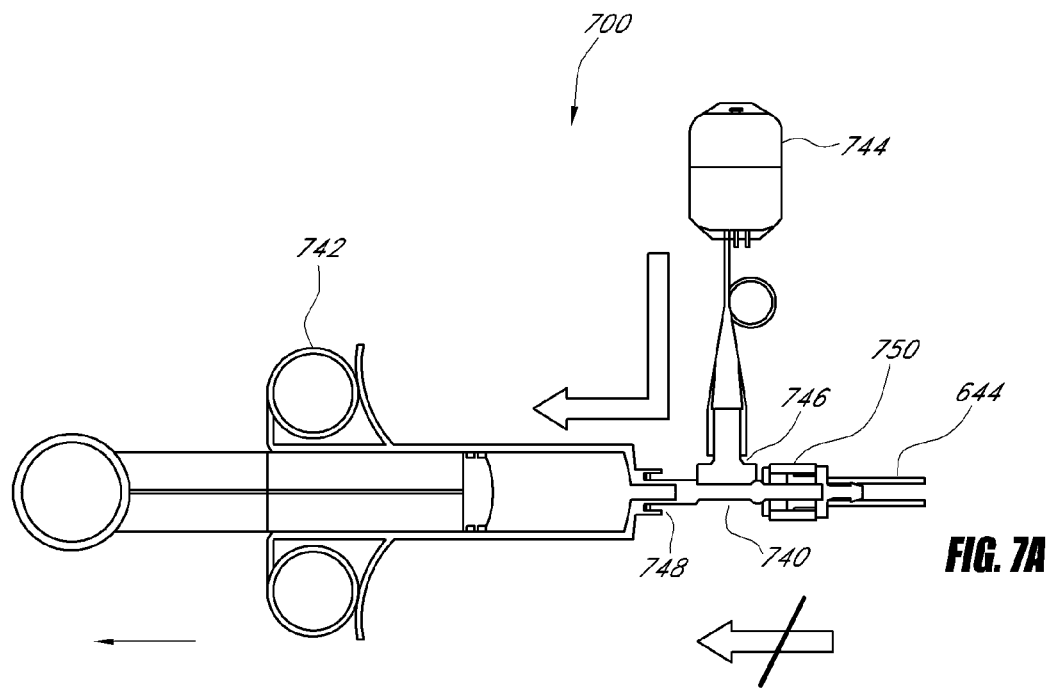
FIGS. 7A and 7B show an example embodiment of a drug delivery system.
Figure 7B:
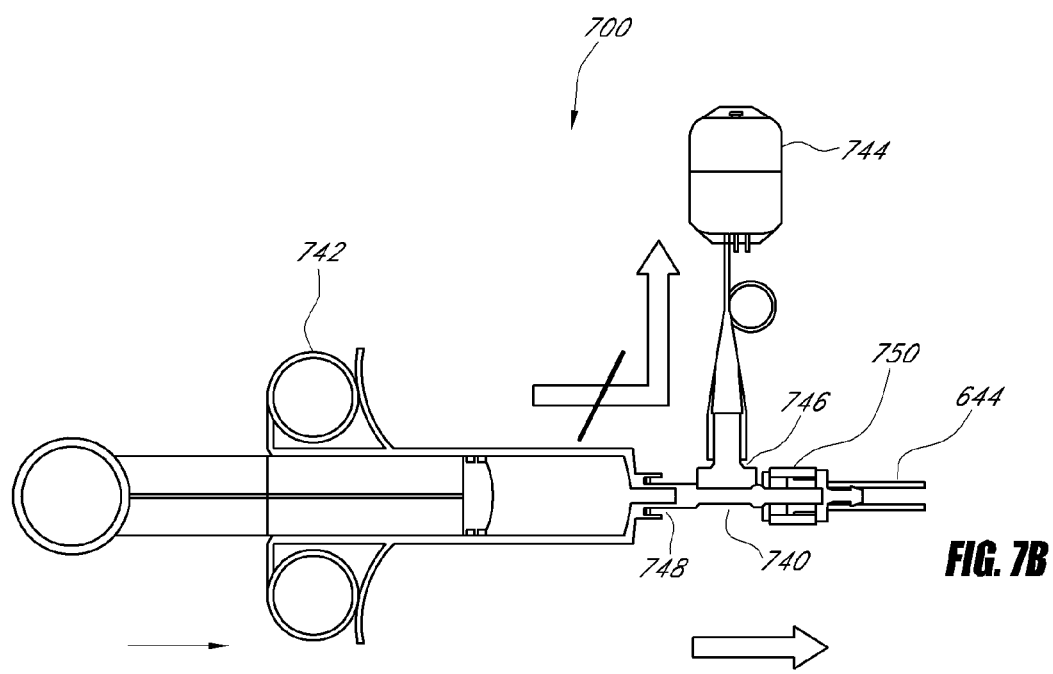

FIGS. 7A and 7B illustrate an example embodiment of a drug delivery system 700 comprising a bi-directional valve 740 coupled to the proximal end of the tubing 644 via a barb (other coupling techniques (e.g., a Luer fitting) are also possible), a syringe 742, and a drug source 744. In some embodiments, the valve 740 comprises a DCV Series double check valve available from Value Plastics®, Inc. of Fort Collins, Colo. The valve 740 can comprise three ports: a chimney port 746 configured to be connected to the fluid supply vessel or drug source 744, an aspiration port 748 configured to be connected to the syringe 742, and a fluid exit port 750 configured to be connected to the tubing 644. The tubing 644 connects the fluid exit port 750 of the valve 740 to the needle 104 or driver 630.

To deliver fluid to the needle lumen and thus to the target tissue, first the plunger of the syringe 742 is pulled back, causing fluid to be drawn from the fluid supply 744 through the chimney port 746, through the aspiration port 748, and then into the syringe 742, as shown in FIG. 7A. The valve to the fluid exit port 750 is pressurized so that fluid (e.g., blood) does not flow from the tubing 644 into the syringe 742. When the plunger of the syringe 742 is then pushed forward, the valve to the chimney port 746 is pressurized so that the fluid cannot travel back through the chimney port 746, and fluid is expelled through the fluid exit port 750 as shown in FIG. 7B.

In some embodiments, the drug delivery system comprises a pump connected to a drug source. In certain such embodiments, the pump is configured to apply positive pressure or zero pressure so that fluid (e.g., blood) does not flow from the needle 104 into the drug source. Other drug supply systems are also possible. The various components of the drug supply system can be connected to each other and the needle or driver via Luer fittings or other appropriate fittings.

Method of Delivering Fluid to Tissue

Figure 8:
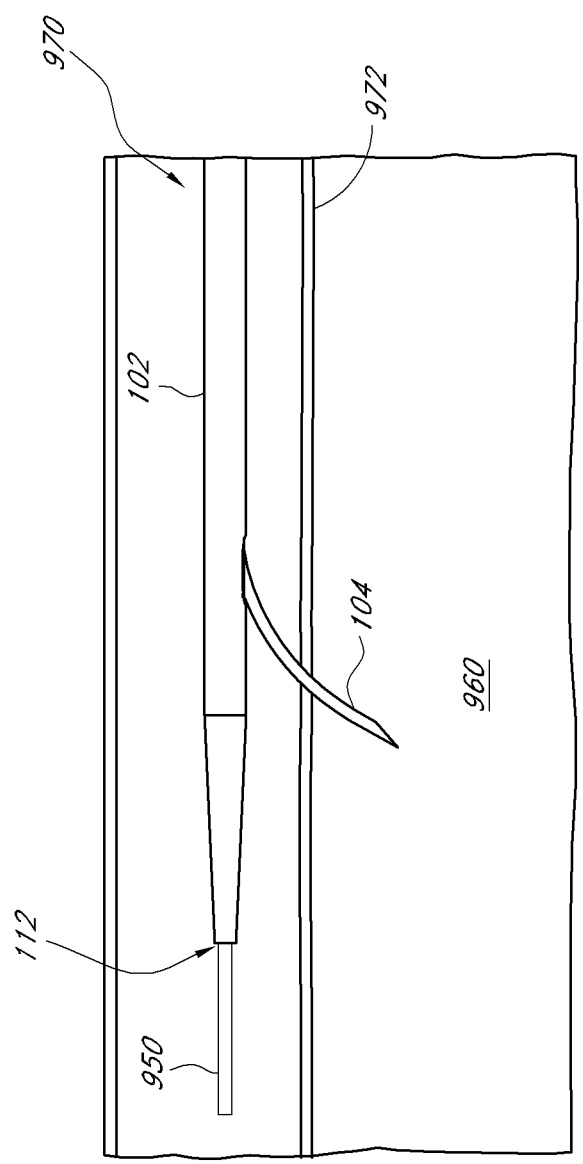
FIG. 8 shows an example embodiment of a method of delivering a fluid to tissue surrounding a body lumen using an endoluminal drug delivery device.
Figure 9:
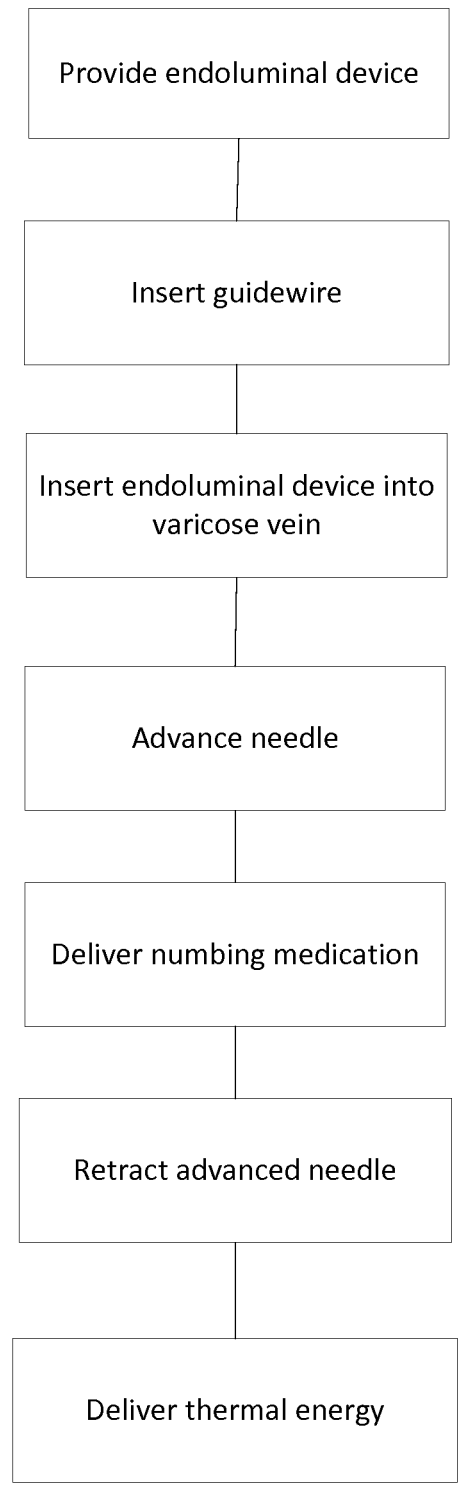
FIG. 9 is a flowchart of a method of delivering a fluid to tissue surrounding a body lumen using an endoluminal drug delivery device.

FIG. 8 shows an example embodiment of a method of delivering a fluid to tissue 960 surrounding a body lumen 970. The method can be performed using an endoluminal drug delivery device 100 and a drug delivery system 700 as described herein. According to some embodiments of the method, a guidewire 950 is percutaneously inserted into the body lumen 970 through the body lumen wall 972, for example, into a varicose or insufficient vein just below the knee. The proximal end of the guidewire 950 is inserted into the opening 112 of the catheter 102, and the distal end 116 of the device 100 is inserted into the body lumen 970 by tracking the first lumen 316 of the catheter 102 over the guidewire 950. When the exit port 106 of the catheter 102 is in a first position, the button 620 on the handpiece assembly 120 outside the body is actuated to cause the distal portion of the needle 104 to exit the catheter 102 through the exit port 106. The needle 104 continues through the body lumen wall 972 and into the target tissue 960. If there is no handpiece assembly 120, the needle 104 is directly manipulated to cause the distal portion of the needle 104 to exit the catheter 102 through the exit port 106 and continue through the body lumen wall 972 into the target tissue 960. A syringe 742 or pump is operated to deliver the drug to the tissue 960. The button 620 on the handpiece assembly 120 is actuated or the needle 104 is directly manipulated to retract the needle 104 back into the catheter 102.

In some embodiments of the method, the device 100 is then again tracked over the guidewire 950 until the exit port 106 is in a second position. The button 620 on the handpiece assembly 120 is again actuated or the needle 104 is directly manipulated to cause the distal portion of the needle 104 to exit the catheter 102 through the exit port 106 and continue through the body lumen wall 972 and into the target tissue 960. The syringe 742 or pump is again operated to deliver the drug to the tissue 960, and the needle 104 is retracted back into the catheter 102. The foregoing process can be repeated for a desired number of positions.

In some embodiments, a method of delivering fluid to tissue can be performed using an endoluminal drug delivery device 100 with multiple exit ports 106*a*-106*n*, as described herein and illustrated in FIG. 3C. Similarly to the method using a single exit port device, a guidewire 950 is percutaneously inserted into the body lumen 970, and the device 100 is inserted into the body lumen 970 by tracking the first lumen 316 of the catheter 102 over the guidewire 950. When the device is inserted into the body lumen 970, the needle 104 is positioned within the catheter such that the distal end of the needle 104 is between the most distal exit port 106*a* and the second exit port 106*b* from the distal end 116 of the catheter 102.

Once the catheter 102 is positioned within the body lumen 970, the button 620 on the handpiece assembly 120 outside the body is actuated to cause the distal end of the needle 104 to exit the catheter 102 through the most distal exit port 106*a*. The needle 104 continues through the body lumen wall 972 and into the target tissue 960. Alternatively, if there is no handpiece assembly 120, the needle 104 is directly manipulated to cause the distal end to exit through the most distal exit port 106*a* and continue through the body lumen wall 972 into the target tissue 960. A syringe 742 or pump is operated to deliver the drug to the tissue 960. The button 620 on the handpiece assembly 120 is actuated or the needle 104 is directly manipulated to retract the needle 104 back into the catheter 102. The catheter 102 is then held stationary within the body lumen, and the needle 104 is moved proximally within the second lumen 318 until the needle 104 exits the second exit port 106*b* from the distal end 116 of the catheter 102. If the device 100 comprises additional exit ports 106, this process can be repeated.

The method of delivering a fluid to tissue surrounding a body lumen 970 can be used, for example, to deliver numbing medication to an area of tissue surrounding a target vein prior to laser or RF ablation treatment for varicose or insufficient veins. In some embodiments, the method of treatment further comprises performing the ablation. The fluid may comprise a drug or anesthetic such as tumescent, which can be, for example, lidocaine possibly in combination with epinephrine, although the exact drug and composition can vary by hospital, provider, patient, and/or treatment.

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosure. Furthermore, dimensions of various components provided herein are exemplary, and other dimensions may be used. Thus, it is intended that the scope of the disclosure herein should not be limited by the particular embodiments described above.

What is claimed is:

1. A method of treating a varicose vein comprising:
    inserting a guide wire into the varicose vein;
    inserting the proximal end of the inserted guidewire through an endoluminal device having at least one lumen and at least one exit port in communication with the at least one lumen so as to insert the endoluminal device into the varicose vein;
    advancing a needle through the exit port so as to pierce the wall of the varicose vein;
    delivering fluid to a target tissue through the advanced needle;
    retracting the advanced needle into the endoluminal device after the fluid has been delivered;
    delivering thermal energy to the varicose vein after the fluid has been delivered so as to cause closure of the varicose vein;
    wherein the at least one exit port includes a plurality of exit ports, further comprising after the step of retracting the advanced needle and prior to the step of delivering thermal energy:
        while holding the inserted endoluminal device stationary, moving the needle to a different one of the exit ports; and
        advancing the needle through the different exit port so as to pierce the wall of the varicose vein;
        delivering the fluid to a different location of the target tissue through the advanced needle; and
        retracting the advanced needle into the endoluminal device after the fluid has been delivered.

2. The method of claim 1, wherein the step of delivering thermal energy includes delivering laser energy to the varicose vein.

3. The method of claim 1, further comprising repeating the steps of advancing a needle through the exit port, delivering fluid to a target tissue and retracting the advanced needle for another target tissue location prior to the step of delivering thermal energy.

4. The method of claim 3, further comprising longitudinally moving the endoluminal device to a second position to target the another target tissue location prior to repeating the steps of advancing a needle through the exit port, delivering fluid to a target tissue and retracting the advanced needle.

5. The method of claim 1, wherein:
    the at least one lumen includes a first lumen and a second lumen in communication with the exit port;
    the step of inserting includes tracking the first lumen over the inserted guidewire.

6. The method of claim 1, wherein the step of advancing a needle includes advancing a needle having a pre-shaped shape memory material such that the needle forms a predetermined curve.

7. The method of claim 1, wherein a section of the endoluminal device distal to the exit port is sufficiently stiff so as to be pushable over the guidewire.

8. The method of claim 1, wherein a section of the endoluminal device distal to the exit port is tapered so as to allow dilation of the vein.

9. The method of claim 1, wherein a section of the endoluminal device distal to the exit port is sufficiently stiff so as to be pushable over the guidewire and is tapered so as to allow dilation of the vein.

10. The method of claim 1, wherein the step of delivering thermal energy includes delivering radio frequency energy to the varicose vein.

11. The method of claim 1, wherein:
    a handpiece assembly is coupled to a proximal end of the endoluminal device, the handpiece assembly including a button coupled to the needle; and
    the step of advancing the needle through the wall to the tissue includes actuating the button.

12. The method of claim 1, wherein the needle comprises a shape memory material.

13. The method of claim 12, wherein the needle comprises nitinol.

* * * * *